(12) United States Patent
Higuchi et al.

(10) Patent No.: US 6,234,959 B1
(45) Date of Patent: May 22, 2001

(54) ELECTRONIC-ENDOSCOPE LIGHT QUANTITY CONTROLLING APPARATUS

(75) Inventors: Mitsuru Higuchi; Shinji Takeuchi; Kazuhiro Yamanaka, all of Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/262,053

(22) Filed: Mar. 4, 1999

(30) Foreign Application Priority Data

Mar. 5, 1998 (JP) .................................................. 10-071324

(51) Int. Cl.[7] ....................................................... A61B 1/06
(52) U.S. Cl. ............................. 600/180; 600/178; 348/69
(58) Field of Search ..................................... 600/103, 160, 600/178, 180, 181; 348/65, 68–70, 220, 221

(56) References Cited

U.S. PATENT DOCUMENTS 5,233,416 * 8/1993 Inoue ...................................... 348/70
6,078,353 * 6/2000 Yamanaka et al. ...................... 348/65

* cited by examiner

Primary Examiner—John Mulcahy
(74) Attorney, Agent, or Firm—Snider & Associates; Ronald R. Snider

(57) ABSTRACT

The present invention is an electronic-endoscope light quantity controlling apparatus that can reduce costs by simplifying a configuration for setting a shielding period in executing an all-pixel reading system. This apparatus uses diaphragm controlling circuit to control a diaphragm so as to maintain the brightness of an image at a predetermined value. It completely closes the diaphragm to set the shielding period and uses this period to form a still image based on the all-pixel reading method. For a moving image, it forms an image signal using a pixel mix reading system at the output of an image pickup device. That is, for a still image, during the shielding period set by the diaphragm, odd-line signals are read out from all pixels obtained by a CCD during a single exposure within a $\frac{1}{60}$-second period, and during the next period, even-line signals are read out from these pixels. Subsequently, a mixing circuit pixel-mixes these line signals into a field signal to form a high-quality still image.

2 Claims, 5 Drawing Sheets

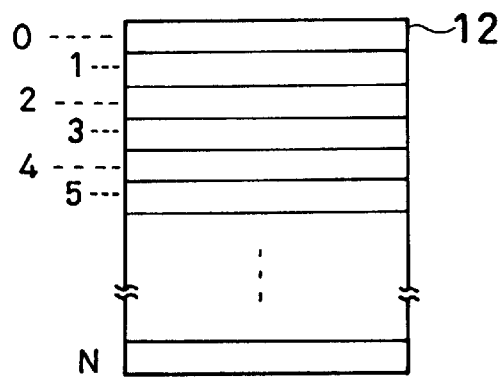
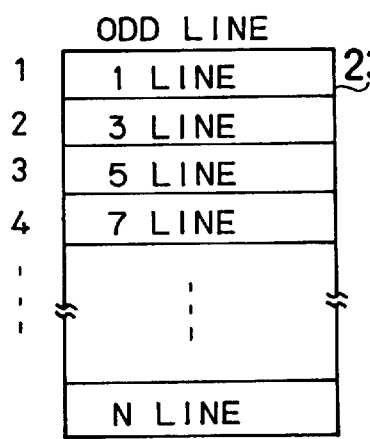
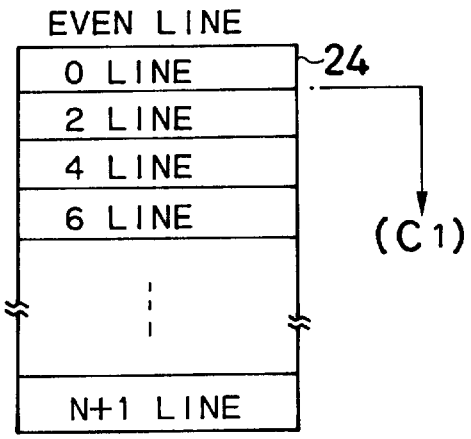
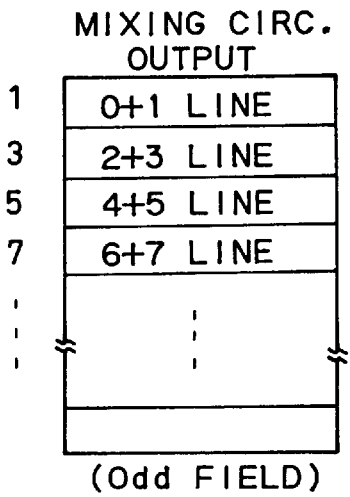
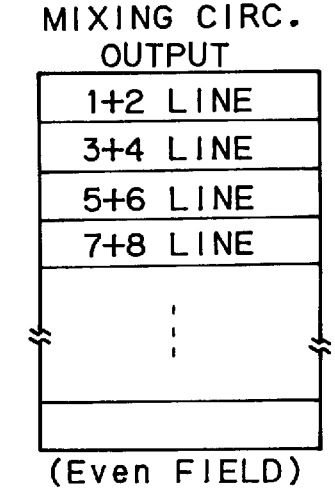

ELECTRONIC-ENDOSCOPE LIGHT QUANTITY CONTROLLING APPARATUS

BACKGROUND OF THE INVENTION

This application claims the priority of Japanese Patent Application No. 10-71324 filed on Mar. 5, 1998 which is incorporated herein by reference.

The present invention relates to an electronic-endoscope light quantity controlling apparatus, and in particular, to the contents of light source unit that can set the shielding period to execute the all-pixel reading system that can read out all the pixels accumulated in the image pickup device.

DESCRIPTION OF THE PRIOR ART

In an electronic-endoscope apparatus, for example, CCD (Charge Coupled Device) is used as a solid image-pickup device, and this CCD is structured so as to obtain an image signal (video signal) by reading out charge accumulated in units of pixels by a photoelectric conversion device. In, for example, a simultaneous type electronic-endoscope apparatus, color filters are arranged in units of pixels on the top surface of the forgoing CCD to thereby obtain a color image.

FIG. 5 shows an arrangement state for the forgoing color filters, and Mg (magenta) and Cy (cyan) pixels are arranged on, for example, an even line, and G (green) and Ye (yellow) pixels are arranged on an odd line on a picked-up surface of CCD1 as shown. In this CCD1, accumulated charge (pixel signal) in units of pixels is to be obtained through these color filters.

According to a conventional color difference line sequential mix reading (pixel mix reading) system, accumulated charges of pixels on the upper and lower lines are added and mixed to be readout. For example, during first exposure, video signals of such odd field as a mixed signal of 0-line and 1-line, a mixed signal of 2-line and 3-line, . . . are readout, and during the second exposure, video signals of such even field as a mixed signals of 1-line and 2-line, a mixed signal of 3-line and 4-line, . . . are readout. Therefore, two lines of mixed signals of CCD1 become one line of signals of field image, and one odd or even field of data are to be obtained by one exposure.

FIG. 6 shows an operation of signals read out from the foregoing CCD1, and in an electronic-endoscope apparatus, an odd field and an even field are formed on the basis of the O (Odd)/E (Even) signal (field signal) for each $1/60$ second (vertical synchronizing period) as shown in FIG. 6(A). Therefore, as shown in FIG. 6(B), signals are accumulated in accumulation (exposure) time T of an electronic shutter during the forgoing period of $1/60$ second, and the accumulation mixed signal is read out during the next $1/60$ second period. As a result, as shown in FIG. 6(c), an odd field signal, and an even field signal are to be obtained, and for example, the (n−1)th odd field signal becomes mixed signals of (0+1) line, (2+3) line, (4+5) line . . . which are shown on the left of FIG. 21, and the n-th even field signal becomes mixed signals of (1+2) line, (3+4) line, . . . which are shown on the right of FIG. 21.

These odd field signals and even field signals are interlace scanned to be formed as a one-frame image, and this image is displayed as a moving image on a monitor. Also, in the endoscope apparatus, a freeze switch is arranged in the operating unit, and when this freeze switch is depressed, a still image at the time is formed and displayed.

BRIEF SUMMARY OF THE INVENTION

In the foregoing simultaneous type electronic-endoscope apparatus, however, there is a time lag of $1/60$ second between those odd field image and even field image which are used to form the one-frame image as shown in the foregoing FIG. 6(C), and if there is a shake of the endoscope itself, a movement of the object to be observed or the like during this period of time, there is the problem that the image quality (resolution, color shift, etc.) will be deteriorated when the still image is displayed. In other words, in the case of a moving image, it is often better to faithfully reproduce the movement and the like of the subject conversely by the foregoing mix reading system in the CCD1, but in the case of a still image, the resolution will be deteriorated.

Thus, the applicant sets a predetermined light shielding period and uses an all-pixel reading system for reading all pixels out from data obtained during one exposure using this period, then in order to set this shielding period, a shielding plate provided in a light source must be driven with predetermined timings to completely shield the light source. The shielding plate and a driving mechanism therefor, however, are newly added members, which complicate the configuration and increase costs.

The present invention has been achieved in the light of this problem, and its object is to provide an electronic-endoscope light quantity controlling apparatus that can reduce costs by simplifying a configuration for setting a shielding period in executing an all-pixel reading system.

SUMMARY OF THE INVENTION

In order to achieve this object, this invention is characterized by comprising an image pickup device driving circuit for using a shielding period to read out signals for all pixels accumulated in an image-pickup device during a single exposure, a diaphragm for adjusting the quantity of light from a light source, and a diaphragm controlling circuit for variably controlling said diaphragm so as to maintain the brightness of an image at a predetermined value and closing the diaphragm to obtain a complete shielding state.

Another aspect of this invention is characterized by applying the invention of the all-pixel reading system to an electronic-endoscope and forming a moving image using a pixel mix reading system at the output of the image pickup device that mixes together and outputs vertically arranged lines of image signals accumulated in the image pickup device, while forming a still image using the all-pixel reading system that uses the light shielding period to read out signals for all pixels accumulated in the image pickup device during a single exposure period.

Next, how this configuration operates if the all-pixel reading system is executed only during the formation of a still image will be described. This is, in a normal condition under which the freeze switch is not pressed, the pixel mix reading system operating when the image pickup device outputs has been selected, and pixels in two lines read out from the image pickup device as in the prior art are mixed together and output to provide a moving image that reproduces motions of an object faithfully.

When a freeze switch is depressed, the all-pixel reading system is selected to form a still image. In the all-pixel reading system, for example, during a predetermined (the first) period of $1/60$ second (a vertical synchronizing period), charges are accumulated due to exposure (the exposure time is arbitrary), and during the second period (in the next exposure), the odd lines in the image pickup device (CCD) are read out and stored in a predetermined memory. During the third period ($1/60$ second), the remaining even lines are read out and stored in a predetermined memory. To allow the even lines to be read out, the light shielding means intercepts light from a light source during the second period.

That is, if, during the second period during which accumulated charges in the odd lines are sequentially read out, subsequent charges are accumulated, as in the prior art, the remaining even lines cannot be read out. Thus, this invention eliminates the optical output during the second period (shielding period) and reads out the accumulated charges in the even lines during the third period. Thereby, the signals of all pixels of the image pickup device obtained by a single exposure can be read out.

According to this invention, a diaphragm driving mechanism installed to adjust the brightness sets the shielding period. That is, although it is essentially impossible that the diaphragm is fully closed, a diaphragm full-close pulse is output to fully close the diaphragm during the above second period in order to set a complete shielding period.

Next, for example, video signals for the odd lines stored first in the memory are stored in a phase adjustment memory and are delayed by $1/60$ second, and a mixing circuit then executes pixel mix processing between data for the odd and even lines. This image mix processing forms signals equivalent to those obtained by a pixel mix reading system operating when the image pickup device outputs signals, but is distinguished from this system in that it mixes pixels based on data obtained during a single exposure. Pixel mix signals are used to form odd and even field signals, and a still image is displayed based on these video signals. Thus, the still image is formed based on the signals for all pixels obtained during the single exposure and has a high quality.

BRIEF DESCRIPTION OF THE DRAWINGS

FIGS. 2(A) to 2(E) are views showing image data read out between CCD of FIG. 1 and the mixing circuit;

DETAILED DESCRIPTION OF THE PREFERRED EMBODIMENTS

Figure 1:
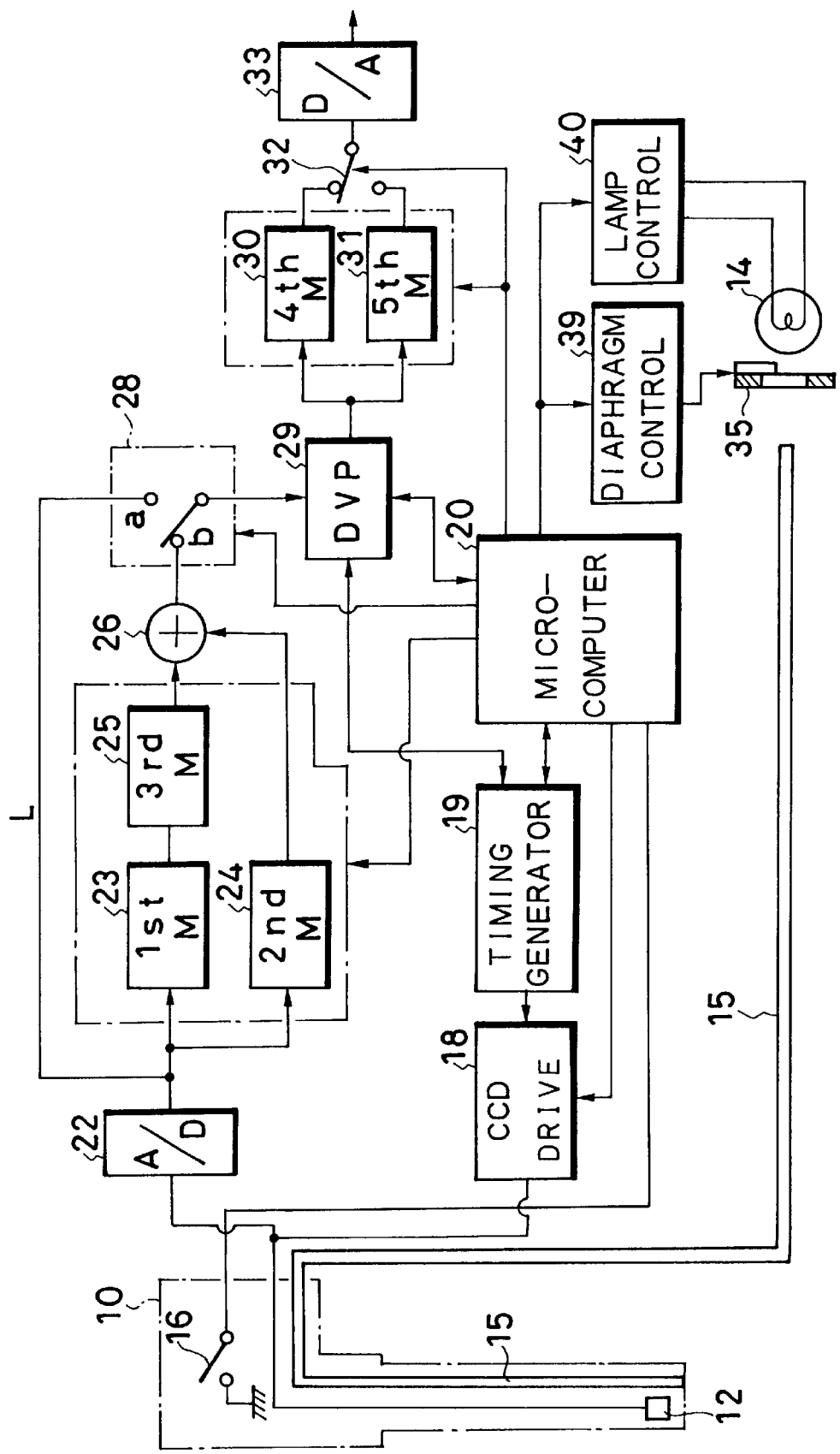
FIG. 1 is a block diagram showing the overall configuration of an electronic-endoscope apparatus according to an embodiment of the present invention.

FIG. 1 shows a circuit configuration of an electronic-endoscope apparatus as an embodiment, this apparatus executes an all-pixel reading system for still images. In FIG. 1, this electronic-endoscope apparatus has such a structure that a scope (electronic-endoscope) 10 is connected to the processor device having an image processing circuit or a light source device (or apparatus obtained by making these devices integral) having a light source. This scope 10 is provided with CCD12 at whose tip end portion the same color filters as described in FIG. 21 are arranged, and with a light guide 15 for guiding light from the light source 14 to the tip end portion. Also, an operating unit for the scope 10 is provided with a freeze switch 16 for displaying a still image.

To the foregoing CCD12, a CCD driving circuit 18 for driving it is connected, and to the driving circuit 18, there are connected a timing generator 19 and a microcomputer 20. To this microcomputer 20, an operation signal from the foregoing freeze switch 16 is inputted. The foregoing CCD driving circuit 18 inputs a timing signal under the control of the microcomputer 20 to control the driving of the pixel mix reading system at the output of CCD for moving images and the all-pixel reading system for still images.

In the case of, for example, the all-pixel reading system, two types of pulses for driving accumulated data for all pixels, which have been accumulated in CCD12 by one exposure, into the odd line and the even line (staggering also temporarily) for reading out, are supplied from the foregoing CCD driving circuit 18, and on the basis of these pulses, control is performed so as to read out the foregoing odd line signals and even line signals from the CCD12 separately and successively. In this respect, one type read pulse is imparted to each line in the pixel mix reading system at the output of CCD.

In addition, after the CCD12 there are provided a first memory 23 for storing image data of the foregoing odd line via an A/D converter 22 in order to read out all pixels, a second memory 24 for storing image data of the even line, a third memory 25 for phase adjustments for storing the data of the foregoing first memory 23 as they are and delaying the read timing by $1/60$ second, and a mixing circuit for still image 26. More specifically, all pixel signals obtained at the CCD12 are divided into data (video signal) of the odd line and data of the even line, and in this state, are once stored in the respective memories 23 and 24, but the odd line data of the first memory 23 are caused to be delayed by $1/60$ second, whereby they are caused to have the same phase as the even line data stored in the second memory 24.

Thus, it becomes possible to read out both image data simultaneously, and in a mixing circuit 26 in the next stage, pixel data of the odd line in the third memory 25 and those of the even line in the second memory 24 can be added and mixed (pixel mixing process for still images). Therefore, in the case of still images, the same pixel mixed signal can be formed as the conventional color difference line sequential mix reading (pixel mix reading) system by this mixing circuit 26.

FIG. 2 shows the content of still image data formed in a circuit from the foregoing CCD12 to the mixing circuit 26. As shown in FIG. 2(A), horizontal lines from 0-line to N-line are provided correspondingly to a number of scanning lines in the CCD12, and the structure is arranged so that the pixel data of these horizontal lines are transferred to a transfer line for reading out. The data of odd lines (1, 3, 5. . . line) in the foregoing CCD12 are stored in the first memory 23 (and the third memory 25) in FIG. 2(B), and the data of even lines (2, 4, 6, . . . line) are stored in the second memory 24 in FIG. 2(C).

The data of these memories 25 and 24 are pixel-mixed between lines in FIGS. 2(B) and 2(C) by the mixing circuit 26 as described above, and as shown in FIG. 2(D), add operation data of 0-line+1-line, 2-line+3-line, 4-line+5-line, . . . are outputted as Odd field data. In a state in which the read line of FIG. 2(C) has been shifted underneath by one line (read out from a position indicated by C1 in the figure), they are pixel-mixed between lines in FIGS. 2(B) and 2(C). As shown in FIG. 2(E), add operation data of 1-line+2-line, 3-line+4-line, 5-line+6-line, . . . are outputted as Even field data. In this respect, in this example, an odd number and an even number in lines of CCD12, and an odd number and an even number in fields for interlaced scanning are distinguished by representing them as ODD, EVEN, and Odd, Even, respectively.

In FIG. 1, at the subsequent stage of the forgoing mixing circuit 26, there is provided an image switching circuit 28 for switching between a moving image and a still image. An output from the A/D converter 22 is supplied to a terminal "a" of the image switching circuit 26 via a line L to form a moving image, while an output from the mixing circuit 26 is provided to its terminal "b". This image switching circuit 28 switches from terminal "a" to terminal "b" by the control of the microcomputer 20 when the forgoing freeze switch 16 is depressed. To this image switching circuit 28, there is connected a digital video processor (DVP) 29, and in this DVP 29, color signal processing using the same pixel mix reading system as before is performed, and for example, a color difference signal or a luminance signal is formed, and control of an image position, enlargement process and the like are performed.

At the subsequent stage of this DVP 29, there are provided a fourth memory 30 for storing odd field data, a fifth memory 31 for storing even field data, a switching circuit 32 for switching between a terminal on the fourth memory 30 side and a terminal on the fifth memory 31 side, and a D/A converter 33. For example, the fourth memory 30 stores odd field data comprising color difference signals into which the data in FIG. 2(D) has been converted, while the fifth memory stores even field data comprising color difference signals into which the data in FIG. 2(E) has been converted.

On the other hand, in a light source unit for supplying light to a light guide 15 arranged in the foregoing scope 10, there are arranged a diaphragm 35 between the foregoing light source (halogen-lamp etc.) 14 and an incident end of the light guide 15. Also, to the foregoing diaphragm 35, a diaphragm control circuit 39 is connected, and to the foregoing lamp 14, a lamp driving circuit 40 is connected. The diaphragm control circuit 39 is adapted to drive the diaphragm 35 on the basis of the luminance signal obtained by the foregoing DVP 29 so as to adjust the quantity of light outputted from the light source 14. And this diaphragm control circuit 39 sets the diaphragm 35 in a complete shielding state for predetermined 1/60 second when the freeze switch 16 is pressed.

Figure 3A:
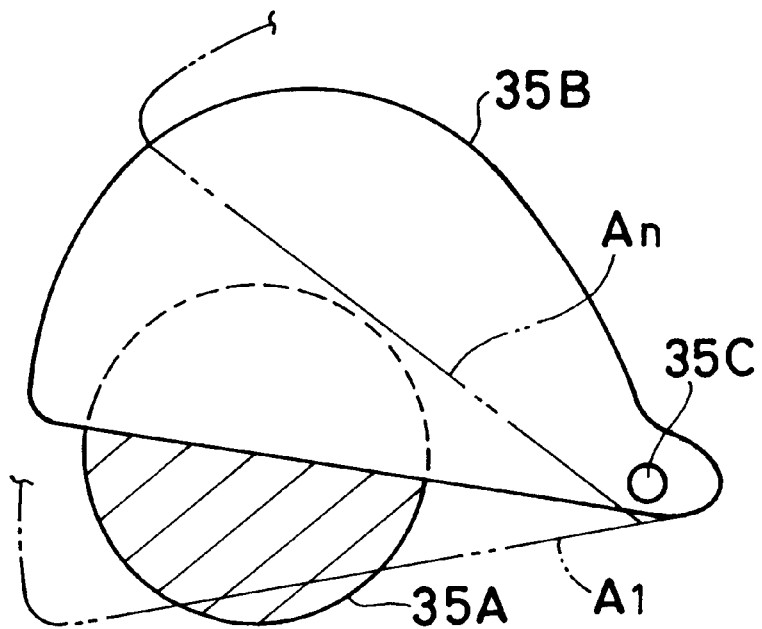
FIGS. 3 is a diagrams showing the configuration of a diaphragm of FIG. 1.

FIG. 3 shows a configuration of the diaphragm 35. The diaphragm 35 includes a diaphragm blade 35B that rotationally moves around 35C in such a way as to intercept a luminous flux (or an aperture) 35A from the light source 14. As shown in FIG. 3(A), iris control that controls the brightness of a normal image can control the numerical aperture, for example, at 20 levels ranging from a minimum aperture position A1 to a full-open position An. In addition, as shown in FIG. 4(B), when all-pixel reading method is selected, the diaphragm blade 35B is driven to a position A0 to completely intercept the luminous flux 35A.

The embodiment is constructed as described above, and the operation will be described with reference to FIG. 4. As shown in FIG. 4(B), a timing signal for forming a one-field image in 1/60 second is used as field O (Odd)/E (Even) signal in the same manner as before. First, under normal conditions, it is set so that moving image processing, that is, the pixel mix reading system at the output of CCD is executed, light from the light source 14 is irradiated from the tip end portion into the object to be observed through the light guide 15.

Figure 5:
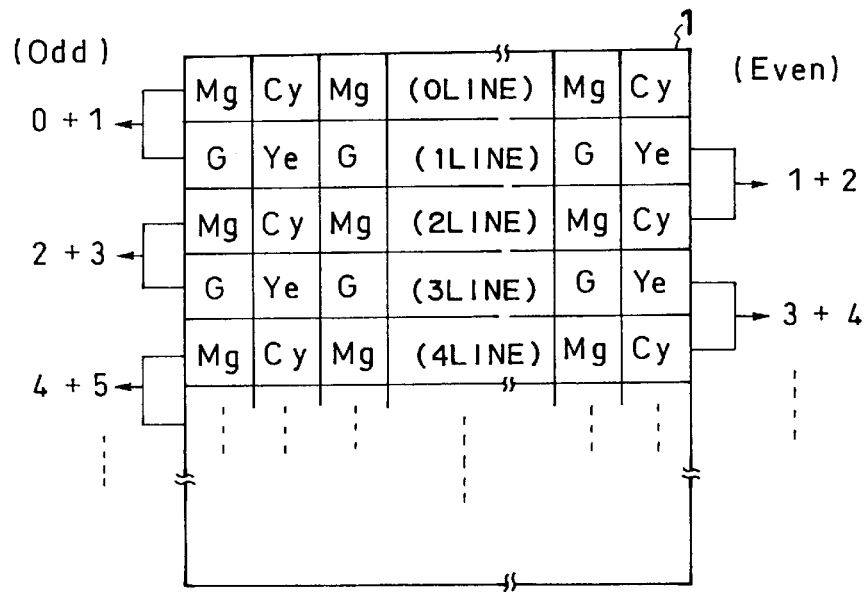
FIGS. 5 describes a configuration of a color filter and a pixel mix readout according to a conventional CCD.
Figure 6:
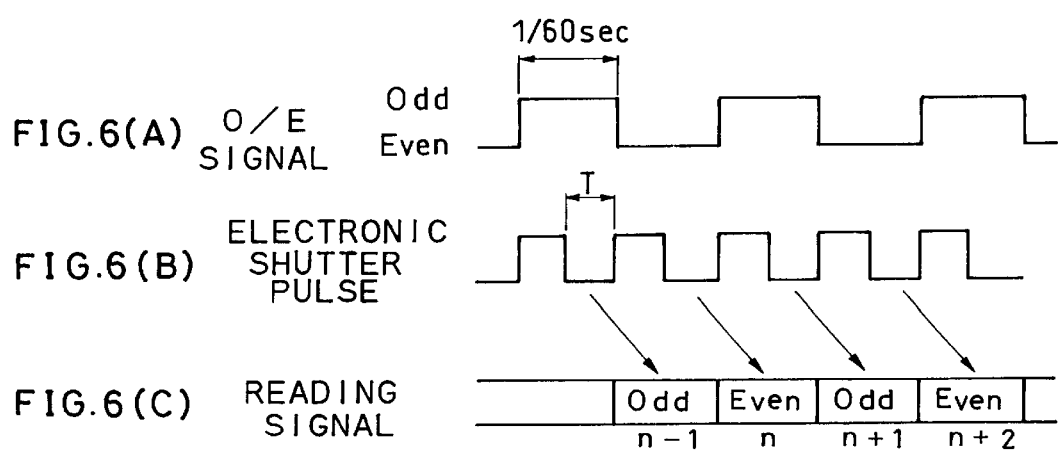
FIGS. 6(A) to 6(C) are explanatory drawings showing an operation performed by a conventional CCD.

By this light irradiation, an image for the object to be observed is obtained in the CCD12 at the tip end portion, and charge corresponding to the image light is accumulated in the CCD12. Pixels between the vertical lines are added to this accumulated charge through a driving pulse from the CCD driving circuit 18 to be read out, and a pixel mixed signal described in FIG. 5 is outputted. This moving image signal is supplied from an A/D converter 22 to an image switching circuit 28 through a through line L. The image switching circuit 28 then switches to the terminal "a" side to supply the moving image signal to the DVP 29.

This DVP 29 forms the color difference signal and the illuminance signal, which is supplied to the microcomputer 20. The microcomputer 20 supplies a control signal for illuminance adjustments to the diaphragm controlling circuit 39. Based on this illuminance control signal, the diaphragm controlling circuit 39 varies the numerical aperture of the diaphragm 35 to maintain the brightness of the image at a predetermined value. In addition, the video signal processed by the DVP 29 is supplied to the fourth and fifth memories 30 and 31 to display a moving image on the monitor based on the odd-field signal stored in the fourth memory 30 and the even-field signal stored in the fifth memory 31.

Figure 3B:
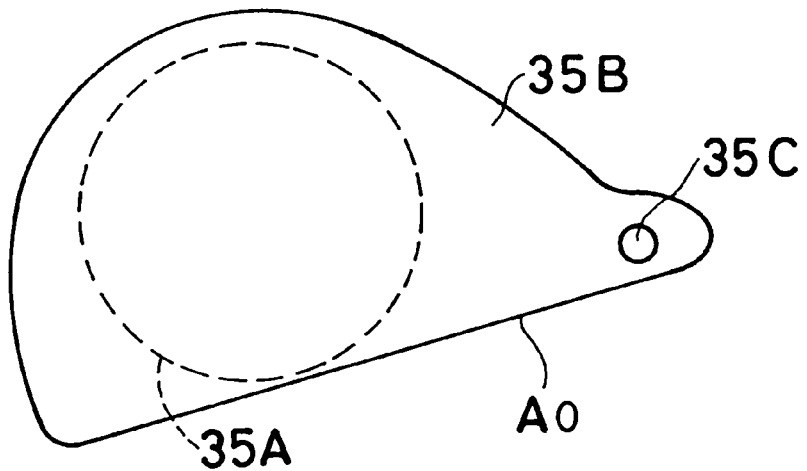

On the other hand, when the freeze switch 16 of the scope 10 in FIG. 1 is depressed, the microcomputer 20 switches the image switching circuit 28 to the terminal "b" side to switch the foregoing pixel mix reading system to the all-pixel reading system for still images by the microcomputer 20. For example, when it is assumed that trigger Tr1 (or Tr2) due to the freeze switch 16 is given as shown in FIG. 4(A), the diaphragm driving pulse forming a diaphragm full-close pulse Pc is output for 1/60 second corresponding to the rise of the next O/E signal between t1 and t2 as shown in FIG. 4(C). As a result, the diaphragm 35B completely intercepts the luminous flux 35A to set this period (t1 to t2) in the shielding state, as shown in FIG. 3(B).

Then, as shown FIG. 4(D), image data, whose all pixels are read out, become charge accumulated in CCD12 by optical output Lt during the immediately preceding period of 1/60 second to the period of time during which the light has been intercepted. The accumulated charges are obtained by the exposure for a portion g1 as shown FIG. 4(G), and the CCD driving circuit 18 reads out the charges for all these pixels.

That is, FIG. 4(E) is a read pulse P1 on the ODD line shown in FIG. 2(B), FIG. 4(F) is a read pulse P2 on the EVEN line shown in FIG. 2(C), and the ODD line data and EVEN line data can be successively read out from the CCD12 according to the read pulse P1 missing a pulse at t3 and the read pulse P2 missing a pulse at t2 as shown in the drawings. Accordingly, the ODD line is read out during the foregoing light shielding period (t1 to t2), and the EVEN line is read out during the next period (t2 to t3). In addition, sweeping is not executed during the light shielding period (t1 to t2) after g1 as shown FIG. 4(G).

The ODD and EVEN line data obtained from the CCD12 using this exposure control are written to the first and second memories 23 and 24 as shown in FIGS. 4(H) and 4(I), respectively, under the control of the microprocessor 20. Next, as shown in FIGS. 4(J) and 4(K), the ODD line data of the first memory 23 and the EVEN line data of the second memory 24 are read out twice each respectively, and the ODD line data are stored in the third memory 25 in order to adjust the phase of 1/60 second. Accordingly, as understood from FIGS. 4(K) to 4(L), the data for the ODD line and those for the EVEN line are to coincide in phase (timing).

Each data read out from the foregoing memories 25 and 24 in this way is pixel-mixed by the mixing circuit 26, and in order to enable this pixel mixing to be performed in this example, the first memory 23 and the second memory 24 are write-inhibited as shown in FIG. 4(M). In the same period as this, the pixels are mixed and converted [FIG. 4(N)], and added data of 0-line+1-line, 2-line+3-line, 4-line+5-line, . .

Figure 4:
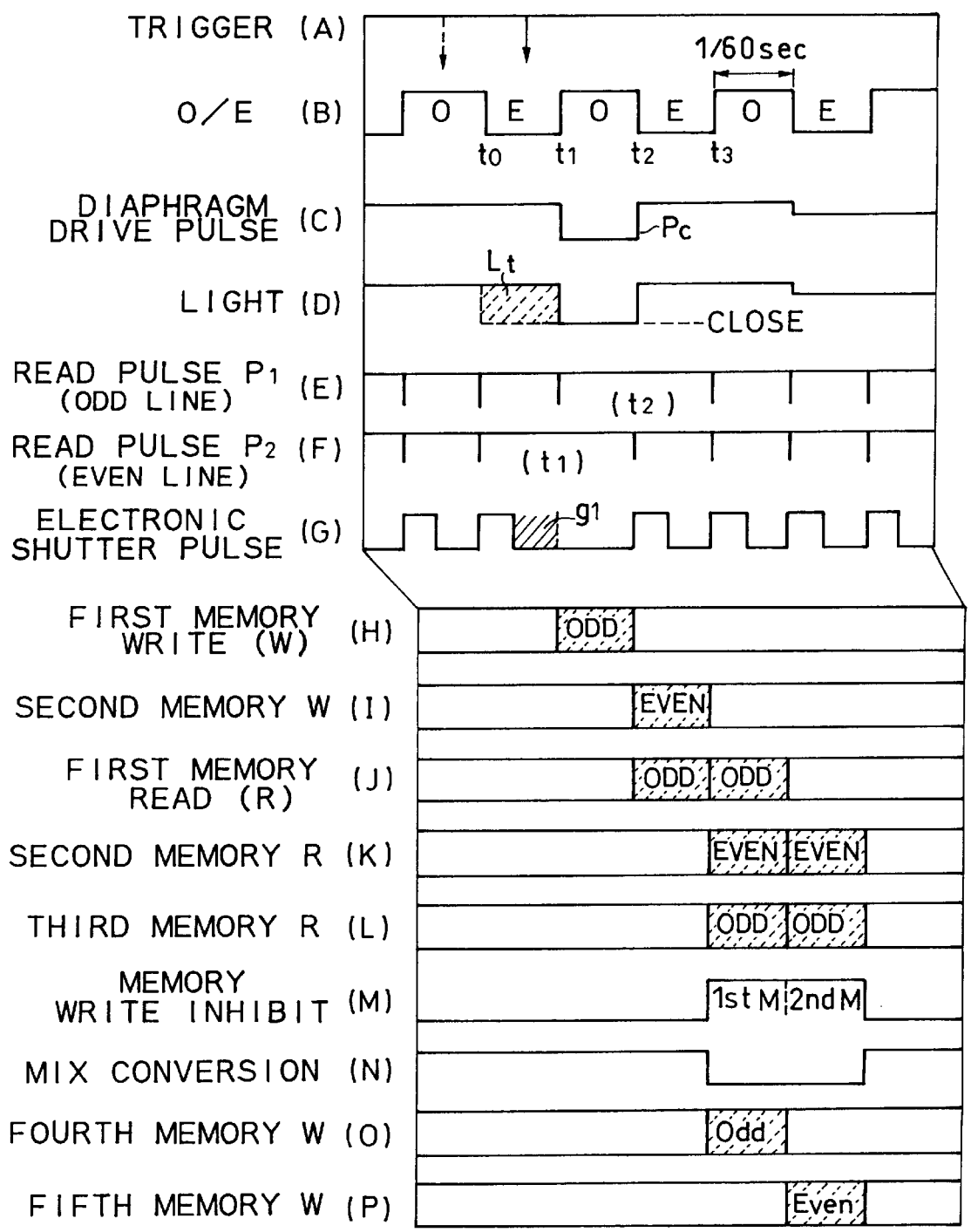
FIGS. 4(B) to 4(P) are explanatory drawings showing a still image formation operation according to the embodiment.

. shown in FIG. 2(D) are first outputted, and are stored in the fourth memory 30 as the Odd field data [FIG. 4(0)]. Next, added data of 1-line+2-line, 3-line+4-line, 5-line+6-line, . . . shown in FIG. 2(E) are outputted, and are stored in the fifth memory 31 as the Even field data [FIG. 4(P)].

The moment when these Odd field data and Even field data are read out, a switching circuit 32 selects the fourth memory 30 and the fifth memory 31 so that each field data is alternately outputted. These field data are outputted to the monitor through a D/A converter 33, and images are displayed on the monitor through interlaced scanning. As a result, as regards still images, the images will be displayed on the basis of the all pixel data obtained during the same exposure, and images with high image-quality and optimal brightness can be obtained. Therefore, even if there is any shake of the endoscope itself in $\frac{1}{60}$ second or any movement of the object to be observed, it, it becomes possible to observe a sharp still image less affected by it.

Furthermore, this embodiment has an advantage of using for a moving image the mix reading system of the CCD1 to enable the movement of an object to be reproduced faithfully. Of course, to make a moving image clearer and completely free from blurring, the all-pixel reading system using the diaphragm 35 and the diaphragm controlling circuit 39 can be used.

As described above, since the embodiment, has a merit which can reduce costs by simplifying a configuration for setting a shielding period in executing an all-pixel reading system.

What is claimed is:

1. An electronic-endoscope light quantity controlling apparatus comprising:

an image pickup device driving circuit for using a complete shielding period to read out signals for all pixels accumulated in an image-pickup device during a single exposure;

a diaphragm for adjusting the quantity of light from a light source; and a diaphragm controlling circuit for variably controlling said diaphragm so as to maintain the brightness of an image at a predetermined value and closing the diaphragm to obtain the complete shielding period.

2. An electronic-endoscope light quantity controlling apparatus comprising:

an image pickup driving circuit for executing a pixel mix reading system at the output of the image pickup device that mixes and outputs vertically arranged lines of image signals accumulated in the image pickup device to form a moving image and an all-pixel reading system that reads out all pixels accumulated in said image pickup device during a single exposure using a complete shielding period set by a light shielding means in order to form a still image;

said light shielding means comprising a diaphragm for adjusting the quantity of light from a light source; and a diaphragm controlling circuit for variably controlling said diaphragm so as to maintain the brightness of an image at a predetermined value and closing the diaphragm to obtain the complete shielding period.

* * * * *